US00PP26237P2

(12) United States Plant Patent
de Groot

(10) Patent No.: US PP26,237 P2
(45) Date of Patent: Dec. 15, 2015

(54) ***HYPERICUM* PLANT NAMED 'RUIHYG234A'**

(50) Latin Name: *Hypericum×Inodorum*
Varietal Denomination: Ruihyg234a

(71) Applicant: Henk C. A. de Groot, Amstelveen (NL)

(72) Inventor: Henk C. A. de Groot, Amstelveen (NL)

( * ) Notice: Subject to any disclaimer, the term of this patent is extended or adjusted under 35 U.S.C. 154(b) by 108 days.

(21) Appl. No.: 13/998,756

(22) Filed: Dec. 3, 2013

(51) Int. Cl.
*A01H 5/02* (2006.01)

(52) U.S. Cl.
USPC ..... Plt./442

(58) Field of Classification Search
USPC ..... Plt./442
See application file for complete search history.

(56) References Cited

PUBLICATIONS

UPOV-PLUTO:Plant Variety Database (International Union for the Protectiion of New Varieties of Plants) Apr. 30, 2015, citation for 'Ruihyg234a'.*

* cited by examiner

*Primary Examiner* — Susan McCormick Ewoldt
(74) *Attorney, Agent, or Firm* — Penny J. Aguirre

(57) ABSTRACT

A new cultivar of *Hypericum×Inodorum*, 'Ruihyg234a', that is characterized by its compact plant habit suitable for container growing, its medium sized berries that are purple-brown in color and ovate in shape and its compact flowers with a flat aspect.

2 Drawing Sheets

Botanical classification: *Hypericum×Inodorum.*
Variety denomination: 'Ruihyg234a'.

BACKGROUND OF THE INVENTION

The present invention relates to a new and distinct cultivar of *Hypericum×Inodorum* and will be referred to hereafter by its cultivar name, 'Ruihyg234a'. 'Ruihyg234a' is a semi-evergreen shrub grown for use as a landscape plant and container plantings.

The new cultivar was derived from a controlled breeding program conducted by the Inventor in Hazerswoude, The Netherlands. The overall purpose of the breeding program was to develop new cultivars of *Hypericum* plants with unique berries and improved resistance to *Melampsora hypericorum.*

The new cultivar arose from a cross made by the Inventor in Hazerswoude, The Netherlands in April 2006 between an unnamed plant from the Inventor's breeding program, designated 'Hp-02-0009-196' as the female parent and 'Annelies Hypearl' (not patented) as the male parent. The Inventor selected 'Ruihyg234a' as a single unique plant amongst the seedlings that resulted from the above cross in 2008.

Asexual propagation of the new cultivar was first accomplished by the Inventor by vegetative stem cuttings in 2009 in Hazerswoude, The Netherlands. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ruihyg234a' as a unique cultivar of *Hypericum.*

1. 'Ruihyg234a' exhibits a compact plant habit suitable for container growing.

2. 'Ruihyg234a' exhibits medium sized berries that are purple-brown in color and ovate in shape.
3. 'Ruihyg234a' exhibits compact flowers with a flat aspect.

The female parent of 'Ruihyg234a', 'Hp-02-0009-196', differs from 'Ruihyg234a' in having berries that are green in color and in having inflorescences that are not as compact and flat. The male parent of 'Ruihyg234a', 'Annelies Hypearyl', differs from 'Ruihyg234a' in having berries that are green in color. 'Ruihyg234a' can be most closely compared to the cultivar 'Bjork Hypearl' (not patented). 'Bjork Hypearl' differs from 'Ruihyg234a' in having orange-brown colored berries that are oval in shape.

BRIEF DESCRIPTION OF THE DRAWINGS

The accompanying colored photographs illustrate the overall appearance and distinct characteristics of the new *Hypericum*. The plants in the photographs were taken of plants two years in age as grown in a one-gallon container in a greenhouse Lelystad, The Netherlands.

The photograph in FIG. 1 provides a side view of 'Ruihyg234a' in bloom.

Figure 1:
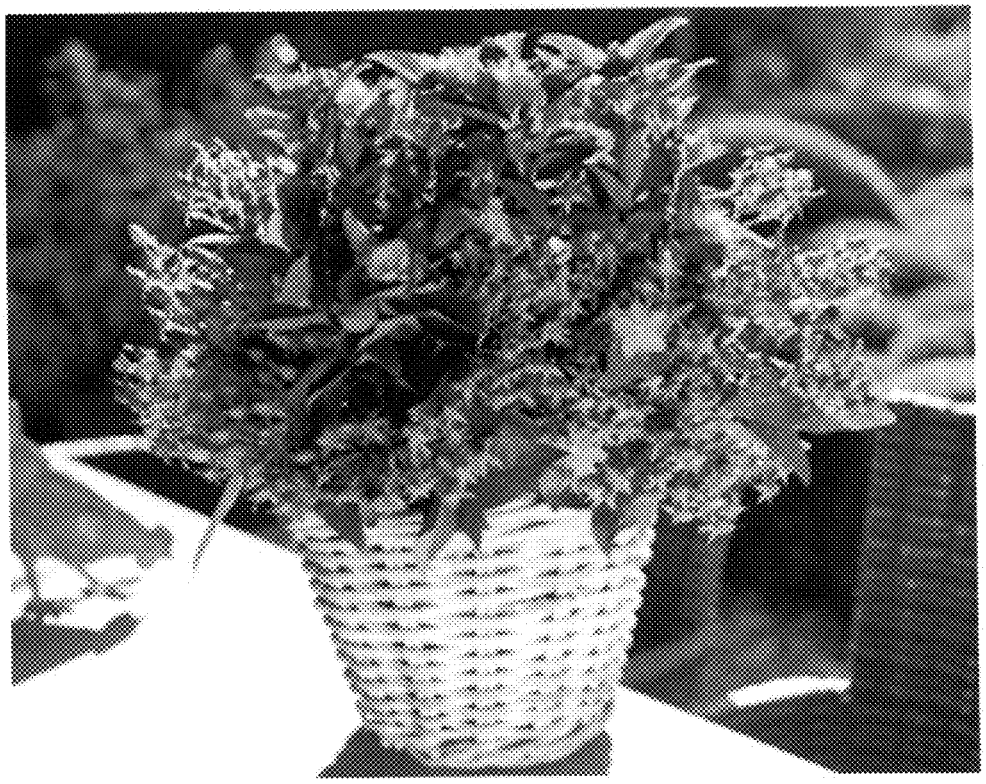
Figure 2:
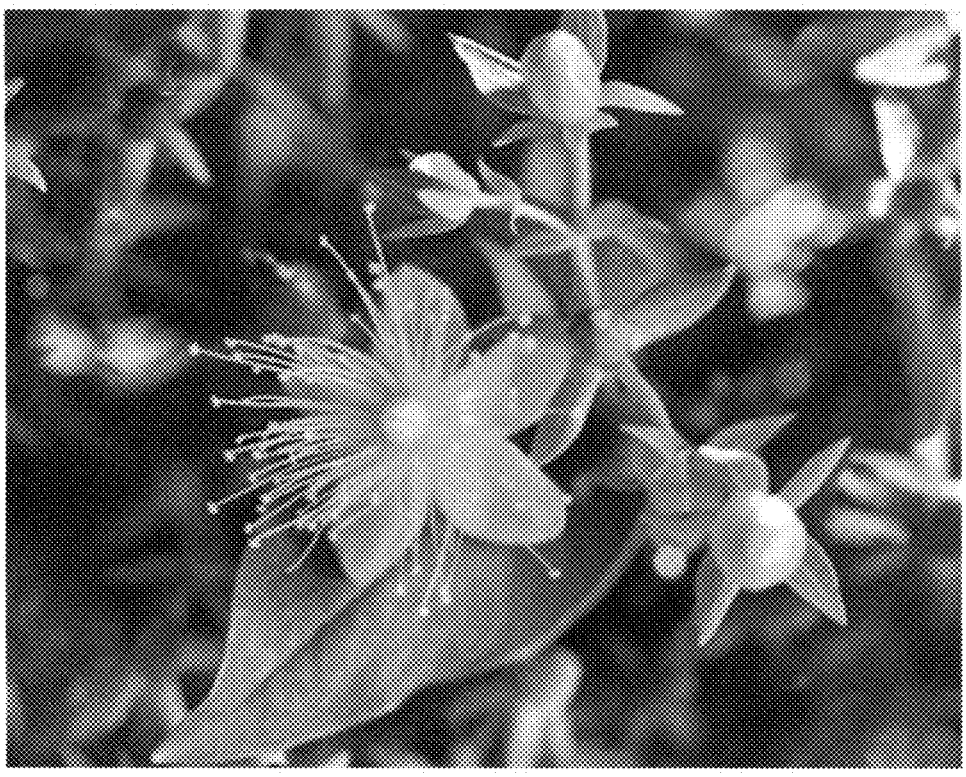

The photograph in FIG. 2 provides a close-up view of a flower of 'Ruihyg234a'.

Figure 3:
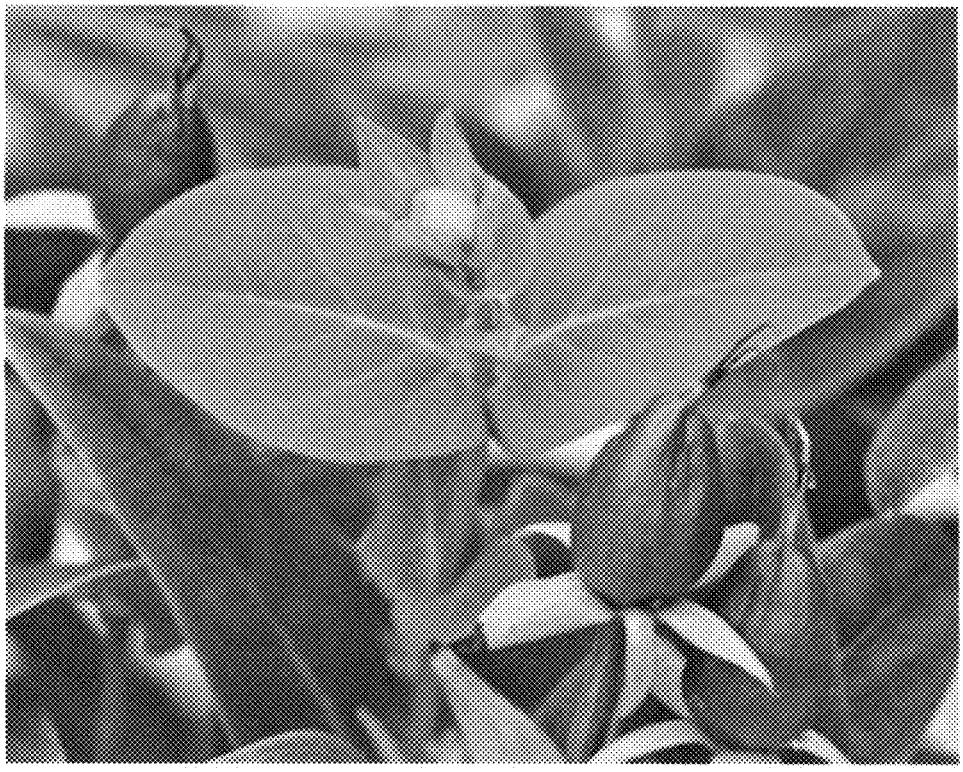

The photograph in FIG. 3 provides a close-up view of a flower bud and berries of 'Ruihyg234a'.

The colors in the photographs are as close as possible with the digital photography techniques available and the color values cited in the detailed botanical description accurately describe the colors of the new *Hypericum.*

DETAILED BOTANICAL DESCRIPTION

The following is a detailed description of two year-old plants the new cultivar as grown outdoors in 2-gallon containers in Davidsonville, Md. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From July to September in The Netherlands.

*Plant type*.—Semi-evergreen shrub.

*Plant habit*.—Compact with suitability for container growing.

*Height and spread*.—Reaches an average of 35 cm in height and 45 cm in spread.

*Cold hardiness*.—Observed to be hardy to at least −10° C.

*Diseases*.—Has shown tolerance to *Melampsora hypericorum*.

*Root description*.—Fibrous and fine.

*Propagation*.—Vegetative stem cuttings.

*Growth rate*.—Moderate, typical for cultivars of *Hypericum×Inodorum*.

Stem description:

*Shape*.—Round.

*Stem color*.—New growth; a blend of 62B and 145C, maturing branches become 199C as they become woody.

*Stem size*.—Main stems; about 3 mm in diameter and 34 cm in length, lateral branches; an average of 30 cm in length and 1.7 mm in width.

*Stem surface*.—Glabrous.

*Internode length*.—Average of 1.5 cm.

*Branching*.—Moderately branched with lateral branches upright to about a 30° angle from vertical.

Foliage description:

*Leaf shape*.—Elliptic to slightly lanceolate.

*Leaf division*.—Simple.

*Leaf base*.—Cuneate.

*Leaf apex*.—Acute.

*Leaf fragrance*.—None.

*Leaf venation*.—Pinnate, slightly conspicuous, 144C on upper surface, 138B to 138C on lower surface.

*Leaf margins*.—Entire.

*Leaf arrangement*.—Opposite, aspect is horizontal to slightly upward.

*Leaf attachment*.—Sessile.

*Leaf substance*.—Moderate.

*Leaf surface*.—Glabrous on upper and lower surface.

*Leaf size*.—Up to about 4.5 cm in length, up to about 1.5 cm in width.

*Leaf color*.—Newly expanded and mature leaves; upper surface a color between 137C and 144A, lower surface 138B.

Inflorescence description:

*Inflorescence type*.—Solitary flowers from terminal of lateral branches.

*Flower buds*.—Conical in shape with acute apex, up to 7 mm in length and 5 mm in width prior to opening, calyx portion is wrapped around petals and 138A in color, petal portion emerges 177A in color and changes to 15A prior to opening.

*Flower fragrance*.—None detected.

*Flower quantity*.—An average of 7 per lateral branch.

*Flower type*.—Complete, compact, rotate with reflexed to horizontal petals and prominent stamens and ovary.

*Flower aspect*.—Upward facing.

*Flower lastingness*.—About 5 days.

*Flower size*.—Average of 2 cm in diameter and 1.5 cm in depth.

*Petals*.—5, narrow oblong in shape, un-fused, curved inward and becoming horizontal, both surfaces glabrous and satiny, entire margin, cuneate base, rounded apex, 1 cm in length and 5 mm in width, color is 15A (opening and mature, lower and upper surface).

*Calyx*.—Reflexed, un-fused sepals, about 1 cm in diameter and 8 mm in depth.

*Sepals*.—5, lanceolate in shape, 138A in color on upper surface and 138B in color on lower surface, glabrous on upper and lower surface, 7 mm length and 4 mm in width, entire margin, round-truncate base, acute-attenuate apex.

*Peduncles*.—Up to 1 cm in length, 1 mm in width, 144A in color, glabrous surface.

*Pedicels*.—About 1 cm in length, 1 mm in width, 144A in color, glabrous surface.

Reproductive organs:

*Gynoecium*.—Compound pistil about 1.5 cm in length and 1.5 cm in width, styles; 3, 187A in color and about 8 mm in length and 0.5 mm in length, stigmas; 3, 187A in color about 0.5 mm in diameter, ovary is superior and 144C in color, about 6 mm in length and 4 mm in width.

*Androcoecium*.—Numerous stamens (about 100, arranged in 5 tufts), spreading outward from base of ovary extending about 2 cm in diameter, filaments are 26A in color, about 8 mm in length and 0.4 mm in width, anthers are 17C in color, dorsifixed, about 1 mm in length and 0.5 in width, pollen is moderate and 17C in color.

*Fruit*.—Ovate in shape with a mucronate apex, glabrous and satiny surface, and average of 9 mm in length and 5 mm in width, a blend of 166A and 183A in color.

It is claimed:

1. A new and distinct cultivar of *Hypericum* plant named 'Ruihyg234a' as herein illustrated and described.

* * * * *